US00PP20275P2

(12) United States Plant Patent
Gray

(10) Patent No.: US PP20,275 P2
(45) Date of Patent: Sep. 8, 2009

(54) ***MANDEVILLA* PLANT NAMED 'SCARLET VELVET'**

(50) Latin Name: *Mandevilla hybrida*
Varietal Denomination: Scarlet Velvet

(76) Inventor: John Gray, P.O. Box 116, Hawthorne, FL (US) 32640

( * ) Notice: Subject to any disclaimer, the term of this patent is extended or adjusted under 35 U.S.C. 154(b) by 0 days.

(21) Appl. No.: 12/148,336

(22) Filed: Apr. 18, 2008

(51) Int. Cl.
*A01H 5/00* (2006.01)

(52) U.S. Cl. ..... Plt./232
(58) Field of Classification Search ..... Plt./323
See application file for complete search history.

*Primary Examiner*—June Hwu

(57) ABSTRACT

A new and distinct *Mandevilla* cultivar named 'Scarlet Velvet' is disclosed, characterized by having distinctive flower coloration, opening pink and turning red, early blooming habit and moderate growth and branching characteristics. The new variety is a *Mandevilla,* normally produced as an outdoor garden or container plant.

1 Drawing Sheet

Figure 1:
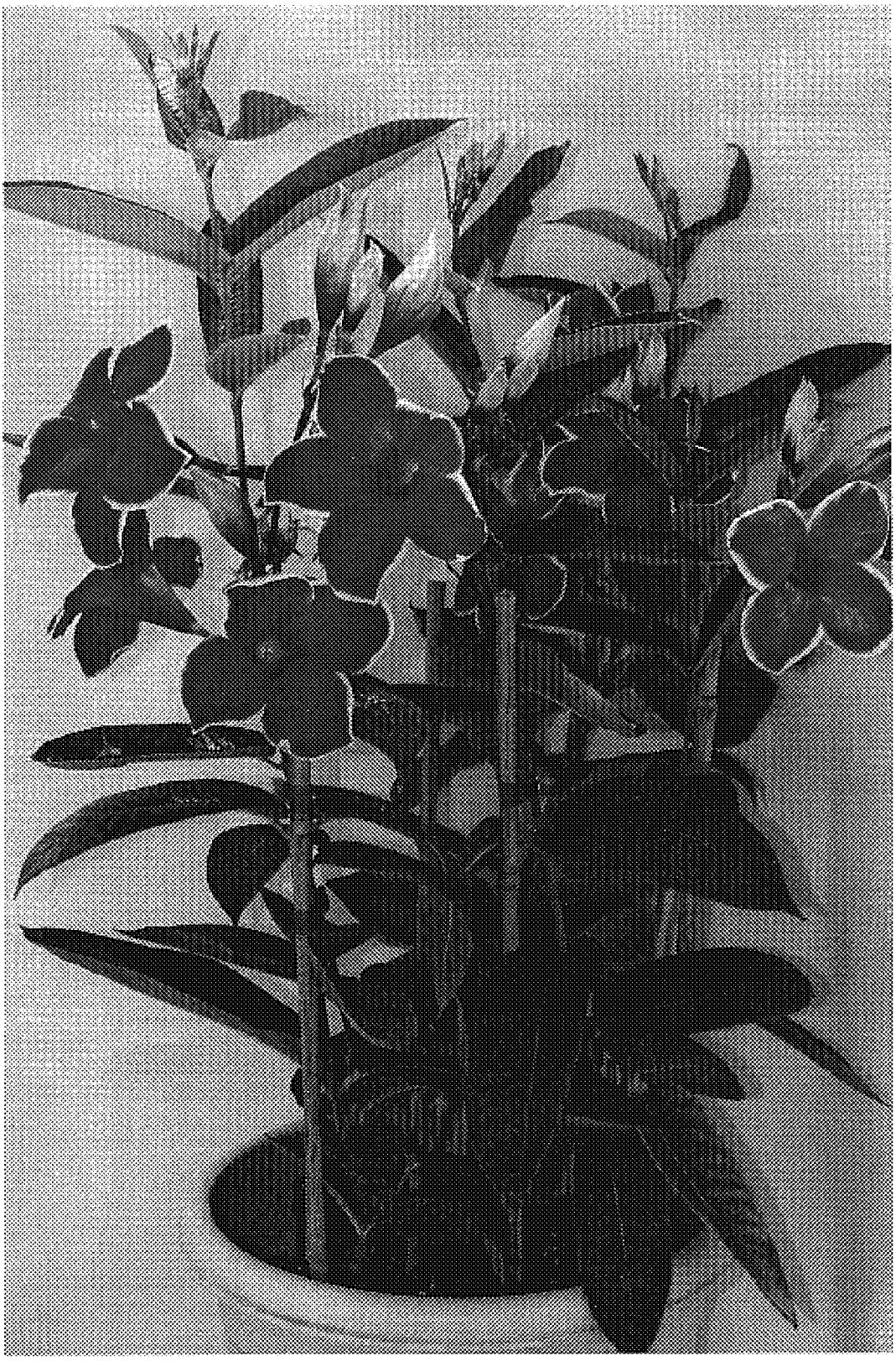

Latin name of the genus and species: *Mandevilla hybrida.* Variety denomination: 'Scarlet Velvet'.

BACKGROUND OF THE INVENTION

The new cultivar is a product of a planned breeding program, with the objective to produce new *Mandevilla* varieties for small pot production. The new variety resulted from a crossing performed in August 2003 in Hawthorne, Fla. The seed and pollen parent is the *Mandevilla* hybrid 'Red Velvet', U.S. Plant Pat. No. 12,238. The new variety was selected April 2006, by the inventor, John Gray in a commercial nursery in Hawthorne, Fla.

Asexual reproduction of the new cultivar 'Scarlet Velvet' by vegetative cuttings was performed at a commercial nursery in Hawthorne, Fla. in June 2006 and has shown that the unique features of this cultivar are stable and reproduced true to type on successive generations.

SUMMARY OF THE INVENTION

The cultivar 'Scarlet Velvet' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'Scarlet Velvet'. These characteristics in combination distinguish 'Scarlet Velvet' as a new and distinct *Mandevilla* cultivar:

1. Distinctive flower coloration, opening pink and turning red.
2. Early blooming.
3. Plant height at blooming of approximately 30 to 45 cm.
4. Moderate branching and growth characteristics.

PARENT COMPARISON

Plants of the new cultivar 'Scarlet Velvet' are similar to plants of the parent variety, *Mandevilla* hybrid 'Red Velvet' in most horticultural characteristics, however, plants of the new cultivar 'Scarlet Velvet' have smaller flowers and smaller leaves. Additionally, 'Scarlet Velvet' flowers earlier than the parent variety.

COMMERCIAL COMPARISON

Plants of the new *Mandevilla* can be compared to the commercial variety 'Sunmandecrim' U.S. Plant Pat No. 15,539. Plants of the new cultivar 'Scarlet Velvet' are similar to plants of 'Sunmandecrim' in most horticultural characteristics, however, plants of the new cultivar have flowers that open pink and turn red, whereas 'Sunmandecrim' open red and remain red. Additionally, the new cultivar has a much less aggressive growth habit than 'Sunmandecrim.'

Plants of the new cultivar can also be compared to the commercial variety 'Red Velvet Petite' U.S. Plant Pat. No. 12,813. 'Scarlet Velvet' is similar to 'Red Velvet Petite' in most horticultural characteristics, however, 'Red Velvet Petite' has an aggressive vining habit, whereas 'Scarlet Velvet' has a moderate vining habit. Additionally, 'Scarlet Velvet' flowers earlier than 'Red Velvet Petite.'

BRIEF DESCRIPTION OF THE PHOTOGRAPH

The accompanying photograph in FIG. 1 illustrates in full color a typical plant of 'Scarlet Velvet' grown in a poly greenhouse with 30% shade, in a 12 cm pot. Age of the plant photographed is approximately 7 months from a rooted cutting. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'Scarlet Velvet' plants grown in a greenhouse in Hawthorne, Fla. The growing temperature ranged from 30° C. to 40° C. during the day and approximately 25° C. at night. The greenhouse is a poly covered with 30% shade. Measurements and numerical values represent averages of typical plant types. No growth retardants were used.

Botanical classification: *Mandevilla hybrida* cultivar 'Scarlet Velvet.'

PROPAGATION

Time to initiate roots: About 15 days at approximately 30° C. in the summer. About 25 days at 18° C. in the winter.
Time to produce a rooted cutting: About 50 days at 20 to 30° C.
Root description: Typical *Mandevilla* root, freely branching and white-brown in color.

PLANT

Growth habit: Vining evergreen flowering plant. Initially upright, then vining, requiring support to maintain upright habit. Typically, plants are pinched approximately 3 months after planting a rooted cutting to encourage branching.
Age of plant described: 7 months.
Container size: 12 cm.
Height: Approximately 25 cm.
Plant spread: Approximately 28 cm.
Growth rate: Moderate.
Branching characteristics: Moderate branching occurs after pinch.
Length of primary lateral branches: Approximately 12 cm.
Diameter of lateral branches: Approximately 0.8 cm.
Internode length: Approximately 3.6 cm.
Stem texture: Very slight pubescence.

FOLIAGE

Leaf:
*Arrangement.*—Opposite, simple.
*Average length.*—Approximately 9 cm.
*Average width.*—Approximately 4.8 cm.
*Shape of blade.*—Elliptic.
*Apex.*—Acute to Cuspidate.
*Base.*—Cordate.
*Attachment.*—Petioled.
*Margin.*—Entire.
*Texture of top surface.*—Very slightly pubescent. Glossy.
*Texture of bottom surface.*—Very slightly pubescent. Matte.
*Leaf internode length.*—Approximately 2.3 cm.
*Color.*—Young foliage upper side: Near RHS Yellow-Green 146A, with a very slight margin of Greyed-Red 181B. Young foliage under side: Near RHS Yellow-Green 146B. Mature foliage upper side: Near RHS Green 137A. Mature foliage under side: Near RHS Green 138B. Some mature leaves have a blush coloration of Red-Purple 71B irregularly occurring on underside.
*Venation.*—Type: Pinnate. Venation color upper side: Near RHS Yellow-Green N144A. Venation color under side: Near RHS Yellow-Green 145C with slight coloration on mid vein of Purple 75C.
*Petiole.*—Average Length: Approximately 1.4 cm. Color: Near RHS Yellow-Green 145B/C. Diameter: Approximately 0.2 cm. Texture: Slightly pubescent.

FLOWER

Natural flowering season: Naturally flower summer through late Autumn.
Inflorescence type and habit: Single salverform flower; terminal or axillary; flowers face mostly outward.
Rate of flower opening: Approximately 6 days from bud to fully opened flower.
Flower longevity on plant: 4 to 5 days, after fully opened. Self-cleaning.
Quantity of flowers: Free flowering, young plants have at least 10 flowers at all times.
Inflorescence size:
*Diameter.*—Approximately 6.9 cm.
*Length.*—Approximately 5.8 cm.
*Corolla tube length.*—Approximately 2.5 cm.
*Throat diameter.*—Approximately 1.8 cm.
Corolla:
*Petal arrangement.*—Single whorl of 5 imbricate petals, fused into flared trumpet.
*Size.*—Lobe Length: 5.9 cm. Lobe Width: 3.1 cm.
*Margin.*—Entire.
*Apex.*—Rounded, slightly undulate.
*Texture.*—Smooth, velvety.
Color: Petals: When opening:
*Upper surface.*—Near RHS Red 53D with steaks of White 155D.
*Lower surface.*—Near RHS Red-Purple 58C with steaks of White 155D.
Fully opened:
*Upper surface.*—Near RHS Red 53C, margin White 155D.
*Lower surface.*—Near RHS Red 53B with steaks and margin of White 155D.
*Tube color.*—Near Red 53C with streaks of White 155D and Yellow-Orange 14C.
*Color changes when aging.*—Color becomes darker, white streaks change to solid red.
Bud:
*Shape.*—Ovate to Lanceolate.
*Length.*—Approximately 5.8 cm.
*Diameter.*—Approximately 1.4 cm.
*Color.*—Near RHS Red-Purple 58B at base, mid bud coloration of Red-Purple 62C and tip of Red-Purple 69D and white.
Sepals:
*Arrangement.*—5 per flower in a single whorl; fused; strongly reflexed.
*Shape.*—Narrowly deltoid.
*Quantity.*—5.
*Length.*—Approximately 0.95 cm.
*Width.*—Approximately 0.4 cm.
*Margin.*—Entire.
*Apex.*—Acuminate.
*Texture.*—Smooth, waxy.
*Color.*—Upper surface: Near RHS. Yellow-Green N144D. Lower surface: Near RHS Yellow-Green N144C/D, flushed with Red-Purple 58A.
Peduncles:
*Length.*—Approximately 1.8 cm.
*Width.*—Approximately 0.3 cm.
*Angle.*—Almost straight.

*Strength.*—Flexible and strong.
*Color.*—Near RHS Red 53C.
Fragrance: None.

REPRODUCTIVE ORGANS

Stamens:
*Number.*—5, anthers fused together at tips, filaments fused to corolla.
*Anther length.*—0.6 cm.
*Anther color.*—Near RHS Yellow 5B.
*Anther shape.*—Oblong.
*Pollen.*—None observed.
Pistil:
*Number.*—1.
*Length.*—Approximately 1 cm.
*Style color.*—Near White 155D.
*Stigma.*—Shape: Rounded. Color: Near RHS White 155D.
*Ovary color.*—Near RHS Yellow-Green 145A.

OTHER CHARACTERISTICS

Seeds and fruits: Not observed to date.
Disease/pest resistance: Neither resistance nor susceptibility to pathogens and pests common to *Mandevilla* have been observed.
Temperature tolerance: Tolerates temperatures from approximately 0° C. to 40° C.

What is claimed is:

1. A new and distinct cultivar of *Mandevilla* plant named 'Scarlet Velvet' as herein illustrated and described.

* * * * *